US012629529B2

(12) United States Patent
Umberger et al.

(10) Patent No.: US 12,629,529 B2
(45) Date of Patent: May 19, 2026

(54) WEARABLE CARDIOVERTER DEFIBRILLATOR CARE SYSTEM WITH HEALTH AND EMOTIONAL COMPANION ACCESSORY

(71) Applicant: WEST AFFUM HOLDINGS DAC, Dublin (IE)

(72) Inventors: Traci Umberger, Kirkland, WA (US); Krystyna Szul, Seattle, WA (US)

(73) Assignee: WEST AFFUM HOLDING DAC, Dublin (IE)

(*) Notice: Subject to any disclaimer, the term of this patent is extended or adjusted under 35 U.S.C. 154(b) by 958 days.

(21) Appl. No.: 17/246,510

(22) Filed: Apr. 30, 2021

(65) Prior Publication Data
US 2022/0054850 A1 Feb. 24, 2022

Related U.S. Application Data

(60) Provisional application No. 63/069,627, filed on Aug. 24, 2020.

(51) Int. Cl.
| | |
|---|---|
| *A61N 1/39* | (2006.01) |
| *A61N 1/372* | (2006.01) |
| *G06N 3/02* | (2006.01) |
| *G06N 20/10* | (2019.01) |

(52) U.S. Cl.
CPC ....... *A61N 1/3904* (2017.08); *A61N 1/37282* (2013.01); *A61N 1/3925* (2013.01); *G06N 3/02* (2013.01); *G06N 20/10* (2019.01)

(58) Field of Classification Search
CPC .............. A61N 1/3904; A61N 1/37282; A61N 1/3925; A61N 1/0484
See application file for complete search history.

(56) References Cited

U.S. PATENT DOCUMENTS

| | | |
|---|---|---|
| 3,724,355 A | 4/1973 | Busch et al. |
| 3,724,455 A | 4/1973 | Unger |
| 4,583,524 A | 4/1986 | Hutchins |

(Continued)

FOREIGN PATENT DOCUMENTS

| | | |
|---|---|---|
| DE | 102005060985 A1 | 6/2007 |
| EP | 2305110 A1 | 4/2011 |

(Continued)

OTHER PUBLICATIONS

Pagan-Carlo, et al., "Encircling Overlapping Multipulse Shock Waveforms for Transthoracic Defibrillation," JACC Journals, Dec. 1998, vol. 32 Issue 7, p. 2065-2071.

(Continued)

*Primary Examiner* — Joseph M Dietrich
(74) *Attorney, Agent, or Firm* — Seed Intellectual Property Law Group LLP

(57) ABSTRACT
A wearable cardioverter defibrillator system supported with a customizable, goal-oriented, companion device. Functionality can be tailored to the goal for a user type. For a patient, the companion device can improve compliance with wear or prescription. Goals can include emotional support, or a specific health, including activity, support. The goal-oriented companion device can receive and process information using machine learning techniques, and interface with a user and other systems and devices.

20 Claims, 10 Drawing Sheets

*SAMPLE COMPONENTS OF WEARABLE CARDIOVERTER DEFIBRILLATOR (WCD) SYSTEM AND COMPANION*

(56)         References Cited

U.S. PATENT DOCUMENTS

| | | | |
|---|---|---|---|
| 4,619,265 A | 10/1986 | Morgan et al. |
| 4,666,432 A | 5/1987 | McNeish et al. |
| 4,698,848 A | 10/1987 | Buckley |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,429,593 A | 7/1995 | Matory |
| 5,474,574 A | 12/1995 | Payne et al. |
| 5,618,208 A | 4/1997 | Crouse et al. |
| 5,662,690 A | 9/1997 | Cole et al. |
| 5,708,978 A | 1/1998 | Johnsrud |
| 5,741,306 A | 4/1998 | Glegyak et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,280,461 B1 | 8/2001 | Glegyak et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 8/2002 | Brack et al. |
| 6,450,942 B1 | 9/2002 | Lapanashvili et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,099,715 B2 | 8/2006 | Korzinov et al. |
| 7,212,850 B2 | 5/2007 | Prystowsky et al. |
| 7,559,902 B2 | 7/2009 | Ting et al. |
| 7,587,237 B2 | 9/2009 | Korzinov et al. |
| 7,753,759 B2 | 7/2010 | Pintor et al. |
| 7,865,238 B2 | 1/2011 | Brink |
| 7,870,761 B2 | 1/2011 | Valentine et al. |
| 7,907,996 B2 | 3/2011 | Prystowsky et al. |
| 7,941,207 B2 | 5/2011 | Korzinov |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,527,028 B2 | 9/2013 | Kurzweil et al. |
| 8,548,557 B2 | 10/2013 | Garstka et al. |
| 8,560,044 B2 | 10/2013 | Kurzweil et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,706,255 B2 | 4/2014 | Phillips et al. |
| 8,742,349 B2 | 6/2014 | Urbon et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,084,583 B2 | 7/2015 | Mazar et al. |
| 9,089,685 B2 | 7/2015 | Sullivan et al. |
| 9,119,547 B2 | 9/2015 | Cazares et al. |
| 9,131,901 B2 | 9/2015 | Volpe et al. |
| 9,132,267 B2 | 9/2015 | Kaib |
| 9,265,432 B2 | 2/2016 | Warren et al. |
| 9,345,898 B2 | 5/2016 | Piha et al. |
| 9,408,548 B2 | 8/2016 | Volpe et al. |
| 9,445,719 B2 | 9/2016 | Libbus et al. |
| 9,454,219 B2 | 9/2016 | Volpe et al. |
| 9,579,020 B2 | 2/2017 | Libbus et al. |
| 9,592,403 B2 | 3/2017 | Sullivan |
| 9,598,799 B2 | 3/2017 | Shoshani et al. |
| 9,675,804 B2 | 6/2017 | Whiting et al. |
| 9,724,008 B2 | 8/2017 | Sullivan et al. |
| 9,878,171 B2 | 1/2018 | Kaib |
| 9,895,105 B2 | 2/2018 | Romem |
| 9,901,741 B2 | 2/2018 | Chapman et al. |
| RE46,926 E | 7/2018 | Bly et al. |
| 10,016,613 B2 | 7/2018 | Kavounas |
| 10,076,656 B2 | 9/2018 | Dar et al. |
| 10,192,387 B2 | 1/2019 | Brinig et al. |
| 10,307,133 B2 | 6/2019 | Kaib |
| 10,463,867 B2 | 11/2019 | Kaib et al. |
| 10,589,110 B2 | 3/2020 | Oskin et al. |
| 10,599,814 B2 | 3/2020 | Landrum et al. |
| 2002/0181680 A1 | 12/2002 | Linder et al. |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0191476 A1 | 7/2012 | Reid et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0144355 A1 | 6/2013 | Macho et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0161554 A1 | 6/2015 | Sweeney et al. |
| 2015/0297135 A1 | 10/2015 | Shoshani et al. |
| 2015/0328472 A1 | 11/2015 | Sullivan et al. |
| 2016/0004831 A1 | 1/2016 | Carlson et al. |
| 2016/0076175 A1 | 3/2016 | Rock et al. |
| 2016/0076176 A1 | 3/2016 | Rock et al. |
| 2016/0082277 A1 | 3/2016 | Foshee, Jr. et al. |
| 2016/0113581 A1 | 4/2016 | Amir et al. |
| 2016/0256104 A1 | 9/2016 | Romem et al. |
| 2016/0283900 A1 | 9/2016 | Johnson et al. |
| 2017/0014073 A1 | 1/2017 | Shoshani et al. |
| 2017/0027469 A1 | 2/2017 | Amir et al. |
| 2017/0036066 A1 | 2/2017 | Chahine |
| 2017/0040758 A1 | 2/2017 | Amir et al. |
| 2017/0162840 A1 | 6/2017 | Pendry |
| 2017/0319862 A1 | 11/2017 | Foshee, Jr. et al. |
| 2017/0367591 A1 | 12/2017 | Jorgensen |
| 2018/0116537 A1 | 5/2018 | Sullivan et al. |
| 2018/0117299 A1 | 5/2018 | Gustavson et al. |
| 2018/0184933 A1 | 7/2018 | Sullivan et al. |
| 2018/0185662 A1 | 7/2018 | Foshee, Jr. et al. |
| 2018/0243578 A1 | 8/2018 | Volosin |

(56) References Cited

U.S. PATENT DOCUMENTS

| | | | |
|---|---|---|---|
| 2018/0361165 A1 | 12/2018 | Jaax et al. | |
| 2019/0030352 A1 | 1/2019 | Sullivan et al. | |
| 2019/0076666 A1 | 3/2019 | Medema | |
| 2019/0116896 A1 | 4/2019 | Armour et al. | |
| 2019/0321650 A1 | 10/2019 | Raymond et al. | |
| 2019/0329055 A1* | 10/2019 | Briscoe | A61B 5/361 |

FOREIGN PATENT DOCUMENTS

| | | | |
|---|---|---|---|
| JP | 4320257 B2 | 8/2009 | |
| JP | 2014526282 A | 10/2014 | |
| JP | 5963767 B2 | 8/2016 | |
| WO | 1998039061 A2 | 9/1998 | |
| WO | 2011/146448 A1 | 11/2011 | |
| WO | 2012/064604 A1 | 5/2012 | |
| WO | 2012/151160 A1 | 11/2012 | |
| WO | 2015/056262 A1 | 4/2015 | |

OTHER PUBLICATIONS

The LifeVest Network/Patient Data Management System, Zoll, 2015, 2000503 Rev A.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Zoll, LifeVest, Proven protection from Sudden Cardiac Death, 2017, 4 pages. Pittsburgh PA, USA.

International Search Report and Written Opinion for PCT Application No. PCT/US2015/051726, dated May 20, 2016, European Patent Office, Rijswijk, 11 pages.

* cited by examiner

SAMPLE COMPONENTS OF WEARABLE
CARDIOVERTER DEFIBRILLATOR (WCD)
SYSTEM AND COMPANION

SAMPLE COMPONENTS OF EXTERNAL DEFIBRILLATOR

COMPONENTS OF
SAMPLE WCD SYSTEM

MULTIPLE ELECTRODES FOR
SENSING ECG SIGNALS ALONG
DIFFERENT VECTORS

SAMPLE COMPONENTS OF A COMPANION

WEARABLE CARDIOVERTER DEFIBRILLATOR CARE SYSTEM WITH HEALTH AND EMOTIONAL COMPANION ACCESSORY

CROSS-REFERENCE(S) TO RELATED APPLICATION(S)

This application claims the benefit of U.S. Provisional Application No. 63/069,627 filed Aug. 24, 2020 entitled Health and Emotional Support Companion, which is expressly incorporated herein by reference in its entirety for all purposes.

BACKGROUND

Some people have a condition or potential risk of a condition in need of monitoring for an extended time and may need to use health monitoring devices. For example, some people have an increased risk of Sudden Cardiac Arrest (SCA). They may include patients who have been determined at risk of an arrhythmia or even already suffered a heart attack, or a prior SCA episode. A frequent recommendation in such cases is to receive an Implantable Cardioverter Defibrillator (ICD). The ICD is surgically implanted in the chest and continuously monitors the patient's intracardiac electrogram (IEGM). If certain types of heart arrhythmias are detected, then the ICD delivers an electric shock through the heart.

As a further precaution, people who have been identified to have an increased risk of SCA can be given a Wearable Cardioverter Defibrillator (WCD) system to wear until an ICD is implanted. Early versions of such systems were called wearable cardiac defibrillator systems. A WCD system typically includes a harness, vest, belt, or another garment that the patient wears. The WCD system further includes electronic components, such as a defibrillator and electrodes, coupled to the harness, vest, or another garment. When the patient wears the WCD system, the electrodes may electrically contact the patient's skin and aid in sensing the patient's electrocardiogram (ECG). If a shockable heart arrhythmia (e.g., ventricular fibrillation or VF) is detected from the ECG, then the defibrillator delivers an appropriate electric shock through the patient's body through the heart. The delivered shock may restart the patient's heart and save the patient's life.

A WCD or an ICD, or other type of wearable or implanted health monitoring and/or treatment system is usually prescribed for an extended time period and a patient's body, and/or the patient physically interacts with the system on daily basis. Such systems are typically intended to process objective physiological signals and do not include a patient or a user experience, or patient/user input as part of the automated system. A patient's or user's experience, along with other patient subjective input, can be valuable indicators and can help improve the quality of care and, in some cases, potentially be very important to the patient outcome. For example, discomfort with a wearable system can lead to frustration, dissatisfaction and also to not wearing a system that could potentially be life-saving altogether.

SUMMARY

This summary is provided to introduce a selection of concepts in a simplified form that are further described below. This summary is not intended to identify key features of the claimed subject matter, nor is it intended to be used as an aid in determining the scope of the claimed subject matter.

The present disclosure describes instances and examples of long-term health monitoring systems with a smart accessory, a health and emotional companion (companion), that complements the long-term monitoring health system or device. The companion, according to some aspects can be customized based on a goal, and can support the system and the patient, by, over time, taking into account data relevant to the achievement of the goal. For example, according to some aspects, companion can be configured to interact with a patient, to respond to, proactively engage, encourage, cheer on, redirect, and/or otherwise support, assist, guide with tasks and/or health-related and/or emotional needs, or goals over an extended period and based on sensor data trend and/or pattern, as well as user subjective input. According to other aspects, a companion can be also customized for other users, depending on the type or function of a user, for example, a clinician, a caregiver, a rescuer, a fitting expert, etc. In other aspects, one or more companion accessories can be used within a network by other types of users, supporting the patient and the monitoring system, such as a WCD system.

DETAILED DESCRIPTION

The description set forth below in connection with the appended drawings is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed. Disclosed herein are embodiments of a health and emotional companion accessory (companion), which can complement long-term health monitoring and/or medical devices or systems.

A wearable cardioverter defibrillator (WCD) system according to some embodiments includes a health and emotional support companion accessory. Patients who use a health monitoring system, such as a WCD or ICD system, can benefit from, and can feel more reassured by, additional physical and/or emotional support, which can lead to a better understanding of user needs and improvements in services provided, and offer an automated, holistic approach to support monitored patients. Such an accessory can process select sensor input along with patient or user input to monitor for patterns, trends, deviations to support achievement of pre-defined health goals and improve overall satisfaction, compliance, and reassurance. Such a WCD system may have a number of components. These components can be provided separately as modules that can be interconnected, or can be combined with other components, and the like.

Figure 1:
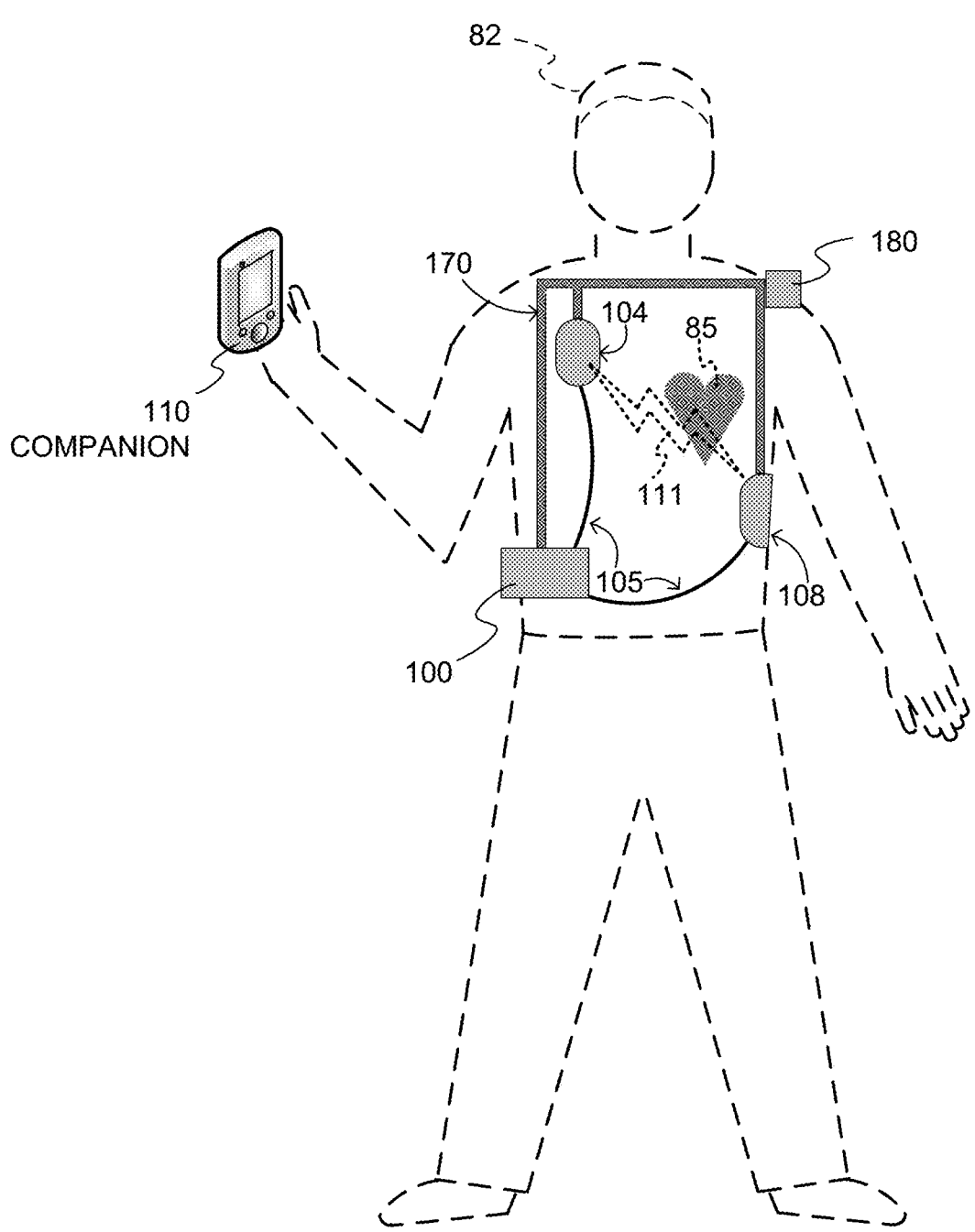
FIG. 1 is a conceptual diagram of a patient wearing a WCD, made according to embodiments.

FIG. 1 depicts a patient 82. Patient 82 may also be referred to as a person and/or wearer, since the patient is wearing components of the WCD system. Patient 82 is ambulatory, meaning while wearing the wearable portion of the WCD system, patient 82 can walk around and is not necessarily bed-ridden. While patient 82 may be considered to be also a "user" of the WCD system, this is not a requirement. For instance, a user of the WCD may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to embodiments can be configured to defibrillate the patient who is wearing the designated parts the WCD system. Defibrillating can be by the WCD system delivering an electrical charge to the patient's body in the form of an electric shock. The electric shock can be delivered in one or more pulses.

In particular, FIG. 1 also depicts components of a WCD system made according to embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In embodiments, support structure 170 could include a vest, a half-vest, a garment, etc. In such embodiments such items can be worn similarly to analogous articles of clothing. In embodiments, support structure 170 could include a harness, one or more belts or straps, etc. In such embodiments, such items can be worn by the patient around the torso, hips, over the shoulder, etc. In embodiments, support structure 170 can include a container or housing, which can even be waterproof. In such embodiments, the support structure can be worn by being attached to the patient's body by adhesive material, for example as shown and described in U.S. Pat. No. 8,024,037, incorporated herein by reference. Support structure 170 can even be implemented as described for the support structure of U.S. Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module or monitor. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of patient 82. Pulse 111 can further include one or more pacing pulses of lesser magnitude to simply pace heart 85 if needed, and so on.

A prior art defibrillator typically decides whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to embodiments can obtain data from patient 82. For collecting such data, the WCD system may optionally include at least an outside monitoring device 180. Device 180 is called an "outside" device because it could be provided as a standalone device, for example not within the housing of defibrillator 100. Device 180 can be configured to sense or monitor at least one local parameter. A local parameter can be a parameter of patient 82, or a parameter of the WCD system, or a parameter of the environment, as will be described later in this document.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also referred to herein as physiological inputs and patient inputs. In embodiments, a sensor can be construed more broadly, as encompassing many individual sensors.

Optionally, device 180 is physically coupled to support structure 170. In addition, device 180 may be communicatively coupled with other components that are coupled to support structure 170. Such communication can be implemented by a communication module, as will be deemed applicable by a person skilled in the art in view of this description.

In embodiments, one or more of the components of the shown WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and so on. Moreover, a programming interface can be made according to embodiments, which receives such measured values of baseline physiological parameters. Such a programming interface may input automatically in the WCD system these, along with other data.

In embodiments, the WCD system includes a companion device 110 (companion). In further embodiments, a companion can have different physical manifestations and can be included in a cell phone, a tablet, a watch, eyeglasses, a gadget, and so on. According to embodiments, companion 110, using machine learning techniques, can be customized based on a goal, and can support the system and the patient, by, over time, for example over the WCD prescription/wear time, taking into account data relevant to the achievement of the goal. In one embodiment, companion 110 comprises a user interface, a companion communication module, and a companion processor. The communication module is configured to communicate with the wearable medical device system, such as the WCD system. The companion can also be configured to communicate with a remote station, and/or other companion devices in the network using the communication module. The companion can be configured to engage the user via the user interface when the processor determines the input is inconsistent with previous data input, or if no communication occurs from the wearable medical device for more than a predetermined period, or has been skipped for a predetermined number of consecutive times, or the quality of the data or communication from the wearable medical device has not been satisfactory, or the data transfer suffered an interruption.

Using machine learning methods, in some embodiments companion 110 can be configured to interact with a patient, to respond to, proactively engage, encourage, cheer on, redirect, and/or otherwise support, assist, guide with tasks and/or health-related, compliance-related, and/or emotional needs, or goals over an extended period and based on sensor data trend and/or pattern, as well as user subjective user input. In some embodiments, companion 110 can be also customized for different types of users, depending on the type or function of a user, for example, a clinician, a caregiver, a rescuer, a fitting expert, etc. One or more companions can be used within a network by other types of users, supporting the patient and the monitoring system, such as a WCD system.

In some embodiments, companion 110 can be configured to use input data aggregated about a user and the system it accompanies over time, which data can include sensor, biometric, visual, and/or auditory input data, the companion can analyze patterns and trends and detect changes, and/or process predictive outcomes and responses and interact with a user.

In some embodiments, companion 110 can include a user interface configured with a natural language recognition function to engage in human-like interactions, and can obtain answers to surveys or answers related to a wellbeing. Embodiments of companion 110 can be configured to, for example, convey patient's responses, which then can be used by the machine learning processing module, as further discussed below, to confirm sensed data determinations, which can be communicated to a caregiver, a designated friend, a centralized care station, or rescuers. In some embodiments, companion 110 can include a user interface customized in creative, interesting and/or entertaining to the user manner so to encourage engagement, use, compliance, or any other goal it is set to achieve/promote, etc.

In some embodiments, companion 110 can include a user interface configured to assist the user with a wearable system and/or product related needs, for example with products that need to be configured, put on, worn, taken off, washed, etc.

Figure 8:
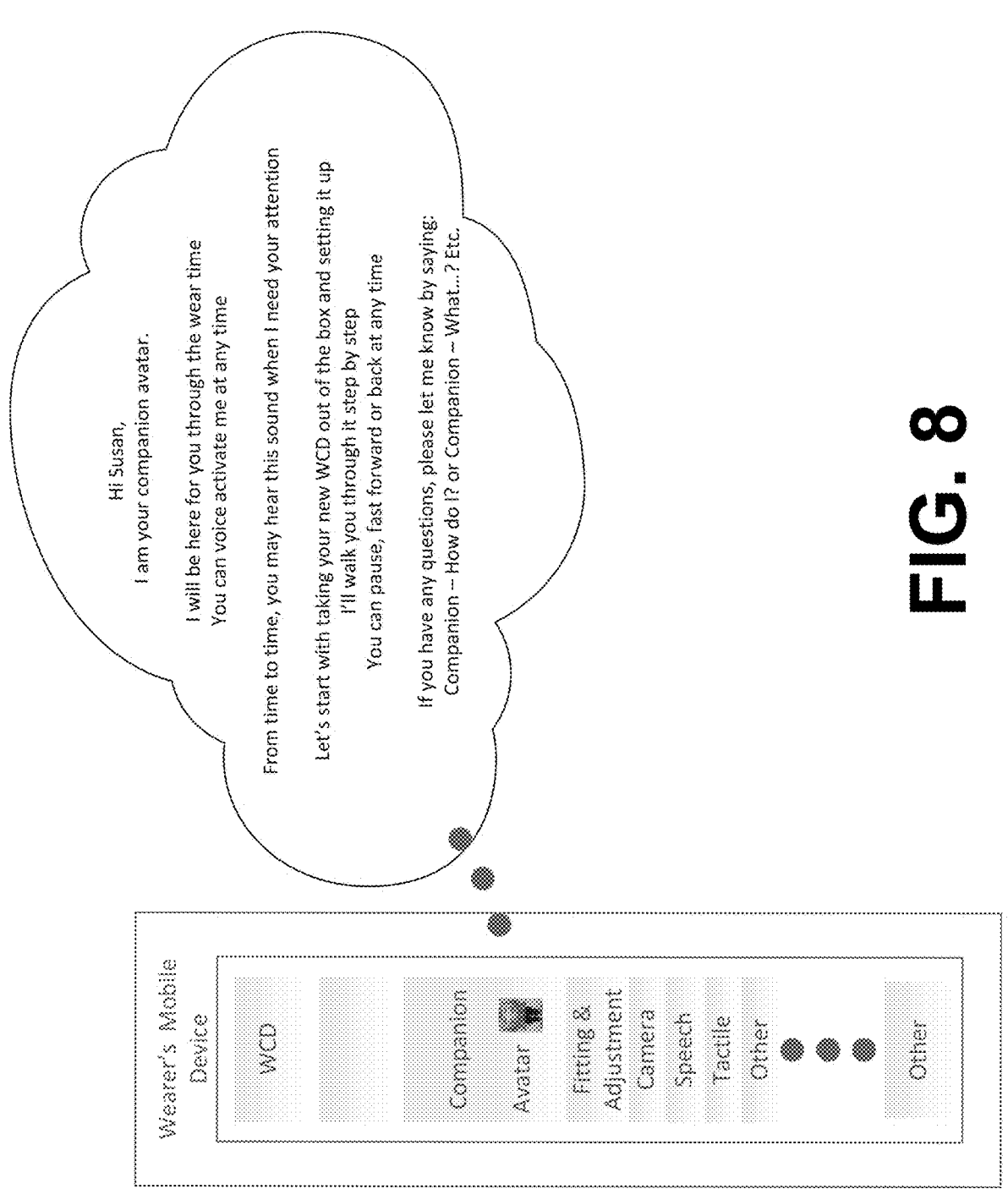
FIG. 8 is an example of a companion avatar implemented on a wearer's mobile device, according to embodiments.

In some embodiments, companion 110 can be an application (app) implementable on a mobile device, or can be a separate physical device or gadget, see FIG. 8. It can be in a form of an avatar, which can be a virtual or augmented reality avatar. The companion can be integrated with AR/VR glasses and interact with an augmented or virtual reality avatar, for example.

In some embodiments, companion 110 can include wireless communication circuitry configured to communicate remotely using and further, optionally being able to switch between Wi-Fi, cellular, and satellite. In further embodiments, companion 110 can include circuitry configured to provide location finding and/or tracking capability. Alternatively, the companion can interact with other devices configured to provide connectivity and communications.

Figure 7:
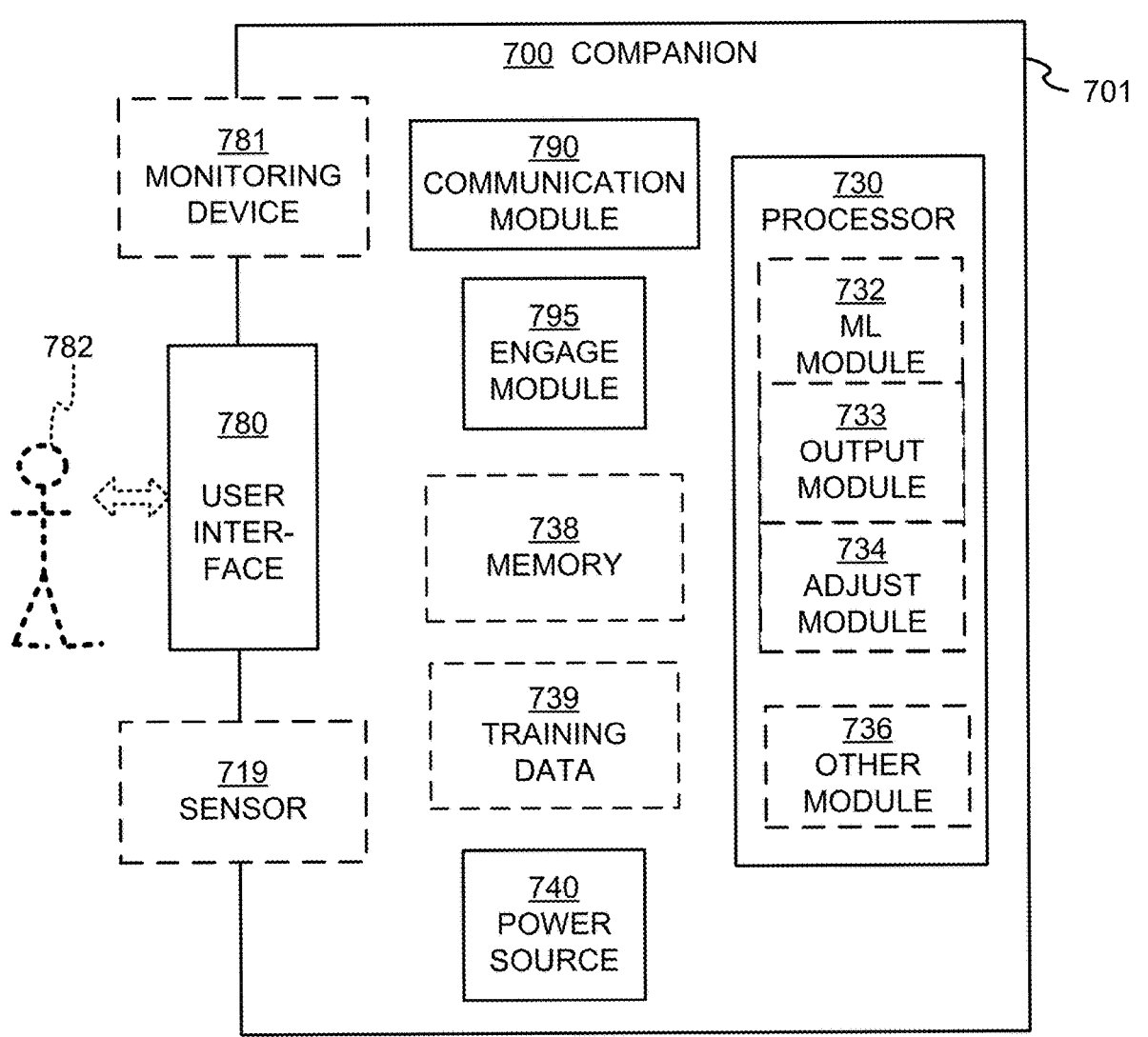
FIG. 7 is diagram of sample components of a companion device, according to embodiments.

In some embodiments, companion 110 can include a processor and machine learning (ML) module with software, see FIG. 7, configured to enable companion 110 to carry out one or more goal-oriented tasks and react to certain data input.

In some embodiments, functionalities can be added, changed, removed as needed, and can be based on a predefined goal for a user. The functionalities can be initially set by a product representative or product expert, or a remote station by taking into account initial patient data from the patient, clinician, monitoring device capabilities, other sensors, etc. For example, for a WCD patient, one of the goals can be to achieve a desirable level of wear compliance. The companion 110 can be programed by fitting expert or a technical expert to assist the patient wearing the WCD with encouragement plans, including wear help, instructions, visual representations of proper wear, avatar help, and rewards for wearing the WCD. To achieve wear compliance goal for a WCD system, the WCD can be configured to send a signal to the companion which may be indicative that the patient is not compliant with the wear. Alternatively, if no data or signal indicative of wear is received by the companion from the WCD over a period of time, for example 24 hours, where such data input or signal is expected, the companion can activate the engage module, see FIG. 7, and attempt to initiate communication with the patient via the user interface of the companion. In a further embodiment, if the communication with the patient cannot be established, for example, there is no response from the patient for a predetermined period of time after the engage module is activated via the user interface, the companion is configured to initiate a communication link with a remote caregiver or remote station communication via the communication module.

Upon establishing response from the patient, the companion 110 can engage the patient to, for example, encourage wear or help determine the cause of noncompliance. The companion 110 can further support the patient in a form of encouragement, by setting up milestones or goals or both for achievement such as continuous WCD wear for a number of days, shortest nonwear overall, and provide reward tokens, compliance trend for a number of days, etc. with the companion and the WCD system.

Based on user status, condition status development, and over time, additional functionalities and goals can be added to the companion 110 and can include social interactions and featuring or sharing success stories, activity level engagement, time interacted with companion, interests, entertainment, emotional or physical wellness, or nutritional habit development and support modules, and so on. Given, for example, a patient's clinician instruction, a user request, progress determined by a monitoring device, determinations of what has been shown to work and what does not for a particular user, status change where a functionality is no longer needed or used, functionalities can be changed to functionalities that better suit the user's and condition's current and future needs. In one example, the companion's machine output module indicates that a user has reached initial goals or milestones and is ready to move onto more advanced level or change in goals entirely. In such situations, the companion can be updated with new functionalities from a clinician-approved list of activities for this user or a menu from a remote station, for example. In another embodiment, a patient refuses to perform certain actions per a functionality provided by the companion, the patient can access a preapproved menu from the companion or a remote location, such as remote station, that can enable machine learning module to switch to processing for the new activity or functionality of the patient. Once goal(s) and means of achieving the goal(s), that is functionalities, are selected, using machine learning methods, the companion can learn, evolve, and refine individualized support by synthesizing information, patterns, trends about the individual it is assigned to over time until the goal(s) are reached.

Figure 2:
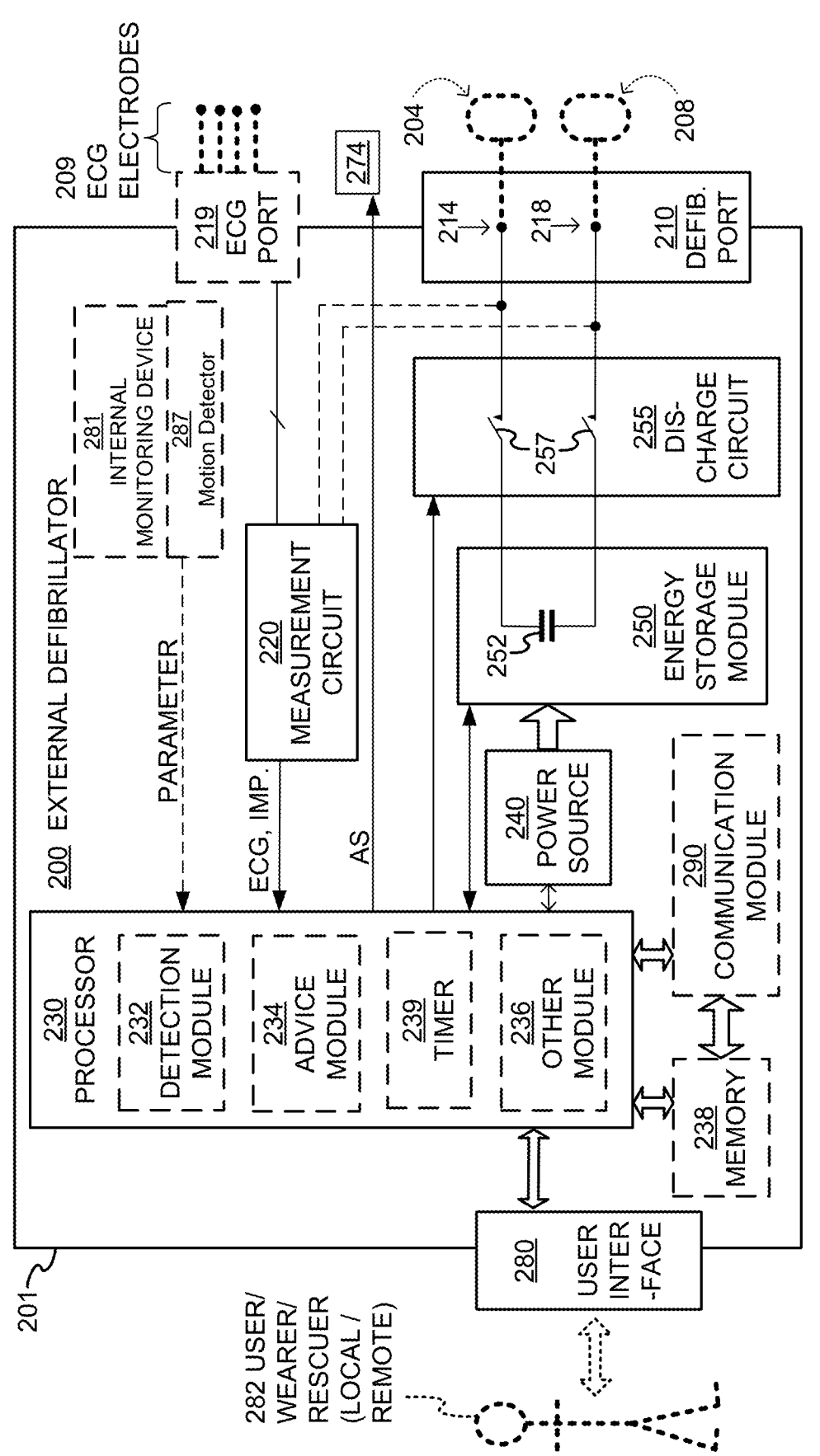
FIG. 2 is a diagram showing components of an external defibrillator, made according to embodiments.

FIG. 2 is a diagram showing components of an external defibrillator 200, made according to embodiments. These components can be, for example, included in external defibrillator 100 of FIG. 1. The components shown in FIG. 2 can be provided in a housing 201, which may also be referred to as casing 201.

External defibrillator 200 is intended to be worn by a patient, such as ambulatory patient 82 of FIG. 1. Defibrillator 200 may further include a user interface 280 for a user 282. User 282 can be patient 82, also known as wearer 82. User 282 could also be a local rescuer at the scene, such as a bystander who might offer assistance, or a trained person. In another embodiment, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device can be a speaker, which can be configured to issue voice prompts, beeps, loud alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document. If internal monitoring device 281 is indeed provided, processor 230 may receive its inputs, etc.

Patient parameters may include patient physiological parameters. Patient physiological parameters may include, for example and without limitation, those physiological parameters that can be of any help in detecting by the WCD system whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds and pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g. a Doppler device), a sensor for detecting blood pressure (e.g. a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on. In view of this disclosure, it will be appreciated that such sensors can help detect the patient's pulse, and can therefore also be called pulse detection sensors, pulse sensors, and pulse rate sensors. In addition, a person skilled in the art may implement other ways of performing pulse detection.

In some embodiments, the local parameter is a trend that can be detected in a monitored physiological parameter of patient 282. A trend can be detected by comparing values of parameters at different times over short and long terms. Parameters whose detected trends can particularly help a cardiac rehabilitation program include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal or gyroscope output and informed from adaptive rate pacemaker technology; d) heart rate trending; e) perfusion, such as from $SpO_2$, $CO_2$, or other parameters such as those mentioned above, f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus may be also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to embodiments may thus include a motion detector. In embodiments, a motion detector can be implemented within monitoring device 180 or monitoring device 281. Such a motion detector can be made in many ways as is known in the art, for example by using an accelerometer and/or a gyroscope. In this example, a motion detector 287 is implemented within monitoring device 281. A motion detector of a WCD system according to embodiments can be configured to detect a motion event. A motion event can be defined as is convenient, for example a change in motion from a baseline motion or rest, etc. In such cases, a sensed patient parameter is motion.

A motion detector, such as motion detector 287 and/or parameter information, such as physiological parameter of patient 282 information can also be used by the WCD to inform another device, such as a companion device 110, shown in FIG. 1, whether the WCD system is being worn. In one embodiment, if the motion detector 287 detects no motion over a period of time, for example 24 hours. The companion, not having received information from the WCD is configured to conclude that the WCD is not being worn. The companion is configured to then engage the patient/ wearer, and optionally also a remote station. On the other hand, when worn, the WCD is configured to detect patient parameters, and periodically sent send information to a remote location using the WCD's communication module 290. When the WCD sends periodic data to a remote station, the WCD also sends to the companion's communication module, see FIG. 7, information that data transfer out of the WCD is occurring and/or has occurred. The companion's processing module is then configured to process this information as information confirming compliance.

In a further embodiment, if the communicated data by the WCD is indicative that leads are off or the garment is not property on or adjusted, or that there is too much noise, or data transfer suffered interruption, for example, the companion can engage the wearer and provide instructions on how to fix the leads off, adjust the garment. If that does not resolve the issue a remote station can be engaged. In one example, the WCD sends data to a remote station, shown in FIGS. 5 and 6. An expert reviews the data. The data appears noisy. The remote station communicates with the companion device via the communication module 790 to engage the patient and if needed, further escalate to engage an expert.

Turning back to defibrillator 200, defibrillator 200 typically includes a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are connected continuously to defibrillation port 210, instead. Either way, defibrillation port 210 can be used for guiding, via electrodes, to the wearer at least some of the electrical charge that has been stored in an energy storage module 250 that is described more fully later in this document. The electric charge will be the shock for defibrillation, pacing, and so on.

Defibrillator 200 may optionally also have a sensor port 219 in housing 201, which is also sometimes known as an ECG port. Sensor port 219 can be adapted for plugging in sensing electrodes 209, which are also known as ECG electrodes and ECG leads. It is also possible that sensing electrodes 209 can be connected continuously to sensor port 219, instead. Sensing electrodes 209 are types of transducers that can help sense an ECG signal, e.g., a 12-lead signal, or a signal from a different number of leads, especially if they make good electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good electrical contact with the patient, similarly with defibrillation electrodes 204, 208.

Optionally a WCD system according to embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being deployed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to embodiments further includes a fluid deploying mechanism 274. Fluid deploying mechanism 274 can be configured to cause at least some of the fluid to be released from the reservoir and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. More strictly speaking, the information rendered by measurement circuit 220 is output from it, but this information can be called an input because it is received as an input by a subsequent device or functionality.

Defibrillator 200 also includes a processor 230. Processor 230 may be implemented in a number of ways in various embodiments. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 230 may include, or have access to, a non-transitory storage medium, such as memory 238 that is described more fully later in this document. Such a memory can have a nonvolatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of executable instructions so as to offer or fulfill a particular functionality. Embodiments of modules and the functionality delivered are not limited by the embodiments described in this document.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful because VF typically results in SCA. Detection module 232 can also include a Ventricular Tachycardia (VT) detector, and so on.

Another such module in processor 230 can be an advice module 234, which generates advice for what to do. The advice can be based on outputs of detection module 232. There can be many types of advice according to embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to embodiments and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In ideal conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. Patent Application No. 2019/0030351, filed on Jul. 17, 2018, and also in U.S. Patent Application No. 2019/0030352, filed on Jul. 17, 2018, both by the same Applicant and both incorporated herein by reference for all purposes.

Processor 230 can include additional modules, such as other module 236, for other functions. In various embodiments, other module 236 may include functional instructions for performing machine learning or artificial intelligence functions. Examples of such functional instructions may be implemented as a neural network, random forest, a support vector machine, recursive partitioning, Bayesian methods, fuzzy rule-based systems, or the like. One or more of such other modules 236 may be configured to implement various embodiments of artificial intelligence functions described below.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory storage medium. Memory 238, if provided, can include programs for processor 230, which processor 230 may be able to read and execute. More particularly, the programs can include sets of instructions in the form of code, which processor 230 may be able to execute upon reading. The programs may also include other information such as configuration data, profiles, scheduling etc. that can be acted on by the instructions. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the inherent needs of processor 230, and can also include protocols and ways that decisions can be made by advice module 234. In addition, memory 238 can store prompts for user 282, if this user is a local rescuer. Moreover, memory 238 can store data. This data can include patient data, system data and environmental data, for example as learned by internal monitoring device 281 and outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices, such as a companion device, see FIG. 7, of other entities, such as a remote assistance center or remote station, Emergency Medical Services (EMS), and so on. The communication links can be used to transfer data and commands. The data may be patient data, event information, therapy attempted, CPR performance, system data, environmental data, and so on. For example, communication module 290 may transmit wirelessly, e.g., on a daily basis, heart rate, respiratory rate, and other vital signs data to a server accessible over the internet, for instance as described in U.S. Patent Publication No. 20140043149. This data can be analyzed directly by the patient's physician and can also be analyzed automatically by algorithms designed to detect a developing illness and then notify medical personnel via text, email, phone, etc. Module 290 may also include such interconnected subcomponents as may be deemed necessary by a person skilled in the art, for example an antenna, portions of a processor, supporting electronics, outlet for a telephone or a network cable, etc. The communication module 290 can send data or signal to another device, such as the communication module 790 of the companion device shown in FIG. 7, at scheduled time intervals that are indicative of wear compliance by a patient.

Defibrillator 200 may also include a power source 240. To enable portability of defibrillator 200, power source 240 typically includes a battery. Such a battery is typically implemented as a battery pack, which can be rechargeable or not. Sometimes a combination is used of rechargeable and non-rechargeable battery packs. Other embodiments of power source 240 can include an AC power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In embodiments, module 250 can be charged from power source 240 to the desired amount of energy, as controlled by processor 230. In typical implementations, module 250 includes a capacitor 252, which can be a single capacitor or a system of capacitors, and so on. In some embodiments, energy storage module 250 includes a device that exhibits high power density, such as an ultracapacitor. As described above, capacitor 252 can store the energy in the form of an electrical charge, for delivering to the patient.

A decision to shock can be made responsive to the shock criterion being met, as per the above-mentioned determination. When the decision is to shock, processor 230 is configured to cause at least some or all of the electrical charge stored in module 250 to be discharged from the defibrillator and into defibrillation electrodes attached to the body of patient 82 while the support structure is being worn by patient 82, so as to deliver a therapy shock 111 to patient 82.

For causing the discharge, defibrillator 200 includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, and so on. Circuit 255 could also be thus controlled via processor 230, and/or user interface 280.

A time waveform of the discharge may be controlled by thus controlling discharge circuit 255. The amount of energy of the discharge can be controlled by how much energy storage module has been charged, and also by how long discharge circuit 255 is controlled to remain open.

In some embodiments, defibrillator 200 can include other components.

Figure 3:
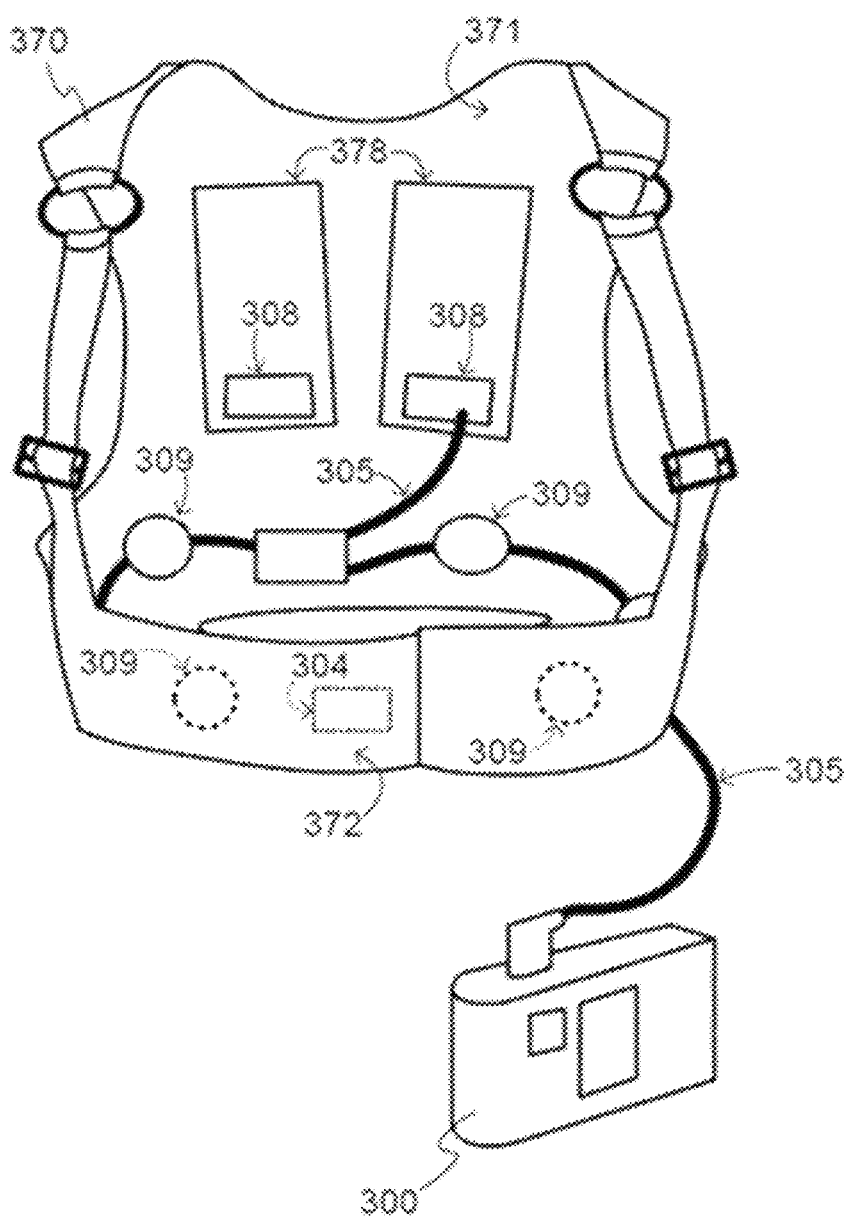
FIG. 3 is a diagram of sample embodiments of components of an WCD system.

FIG. 3 is a diagram of sample embodiments of components of a WCD system. A support structure 370 includes a vest-like wearable garment. Support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the ambulatory patient so as to maintain electrodes 304, 308, 309 on a body of the patient. In some embodiments, back defibrillation electrodes 308 are maintained in pockets 378. In some instances, the inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

ECG signals in a WCD system may include too much electrical noise to be useful. To ameliorate the problem, multiple ECG sensing electrodes 309 are provided, for presenting many options to processor 230. These options are different vectors for sensing the ECG signal, as described now in more detail.

In one embodiment, a device, such as companion device 110, shown in FIG. 1, can be advantageous in addressing the electrical noise issue of the ECG electrodes. For example, when noise is observed, the companion device 110 can be triggered to engage the patient via user interface and provide instructions to the patient on how to remedy the issue, whether it is to remain still or reposition an ECG electrode, or adjust the fit of the support structure. Furthermore, if instructions provided by the companion are not satisfactorily resolving the issue of noise, the companion can communicate to remote station about the issue and additional steps can be performed, for example the remote station expert reach out to the patient or a fitting expert could be engaged or dispatched, if needed. In one example, the WCD sends data to a remote station, as further described in more detail below. An expert reviews the data. If the data appears noisy, the remote station, shown in FIG. 5, for example, can communicate with the companion device via the communication module to engage the patient and suggest possible causes and how to resolve them.

Figure 4:
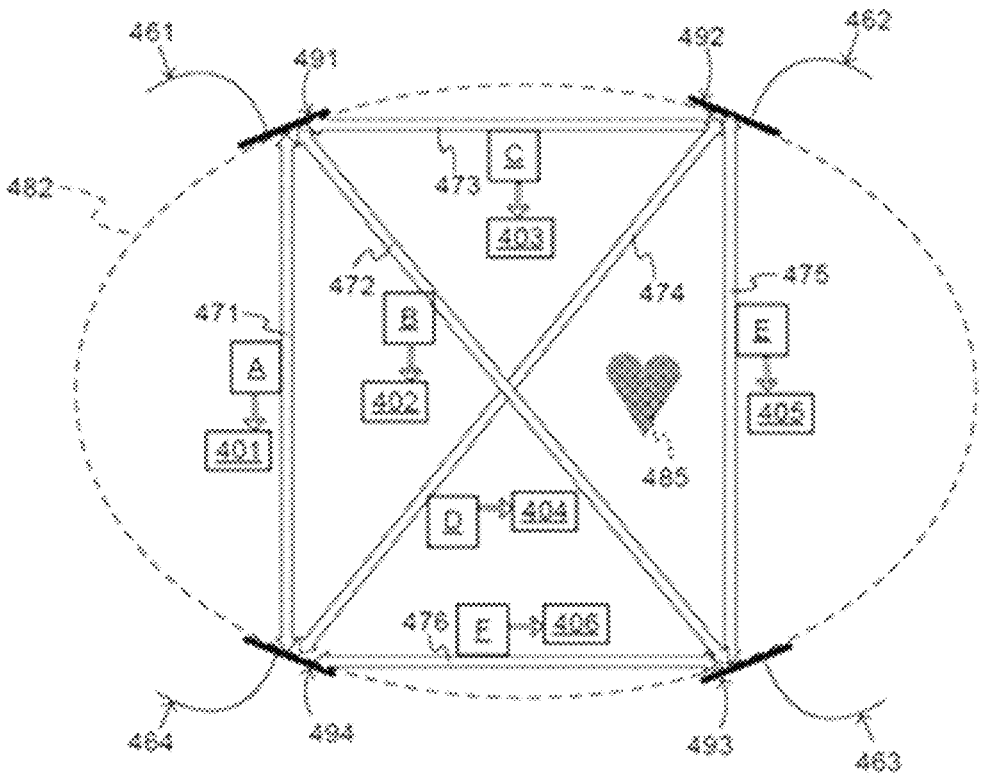
FIG. 4 is a conceptual diagram for illustrating how multiple electrodes of a WCD system may be used for sensing ECG signals along different vectors, according to embodiments.

FIG. 4 is a conceptual diagram for illustrating how multiple electrodes of a WCD system may be used for sensing ECG signals along different vectors according to embodiments. A section of a patient 482 having a heart 485 is shown. In FIG. 4, patient 482 is viewed from the top, patient 482 is facing downwards, and the plane of FIG. 4 intersects patient 482 at the torso of the patient.

Four ECG sensing electrodes 491, 492, 493, 494 are maintained on the torso of patient 482, and have respective wire leads 461, 462, 463, 464. It will be recognized that electrodes 491, 492, 493, 494 surround the torso, similarly with sensing electrodes 309 in the example of FIG. 3.

Any pair of these four ECG sensing electrodes 491, 492, 493, 494 defines a vector, along which an ECG signal may be sensed and/or measured. As such, electrodes 491, 492, 493, 494 define six vectors 471, 472, 473, 474, 475, 476. FIG. 4 thus illustrates a multi-vector embodiment.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

In FIG. 4 it will be understood that electrodes 491, 492, 493, 494 are drawn as being on the same plane for simplicity and as is preferred, while that is not necessarily the case. Accordingly, vectors 471, 472, 473, 474, 475, 476 are not necessarily on the same plane, either.

In embodiments, in order to make the shock/no-shock determination as correctly as possible, a WCD may assess which of ECG signals 401, 402, 403, 404, 405, 406 is best for rhythm analysis and interpretation. For example, ECG signals that have the most noise may be ignored, discarded, not considered, while leaving the remaining ECG signals as candidates for making the shock/no shock determination.

In other embodiments, the vectors may be aggregated to make a shock/no shock decision, and/or to determine the patient's heart rate and/or QRS widths. For example, in some embodiments the aggregation can be implemented as disclosed in U.S. Pat. No. 9,757,581 issued Sep. 12, 2017 entitled "WEARABLE CARDIOVERTER DEFIBRILLATOR COMPONENTS MAKING AGGREGATE SHOCK/ NO SHOCK DETERMINATION FROM TWO OR MORE ECG SIGNALS", which is incorporated herein by reference.

As mentioned with respect to FIG. 3 above, the companion device 110, shown in FIG. 1, can be advantageous in further alleviating the issue of ECG signal noise. When noise is observed, the companion device 110 can provide instructions to the patient on how to remedy the issue, whether it is to hold still while the ECG signals are being acquired or an ECG electrode needs repositioning, etc. Further, if instructions provided by the companion are not satisfactorily resolving the issue of noise, a fitting expert can be engaged or dispatched to the patient. In one example, the WCD sends data to a remote station, as further described in more detail below. An expert reviews the data. The data appears noisy. The remote station can communicate with the companion device via the communication module 790 to engage the patient and suggest possible causes and how to resolve them.

Health and Emotional Support Companion Device (Companion) Embodiments

Figure 5:
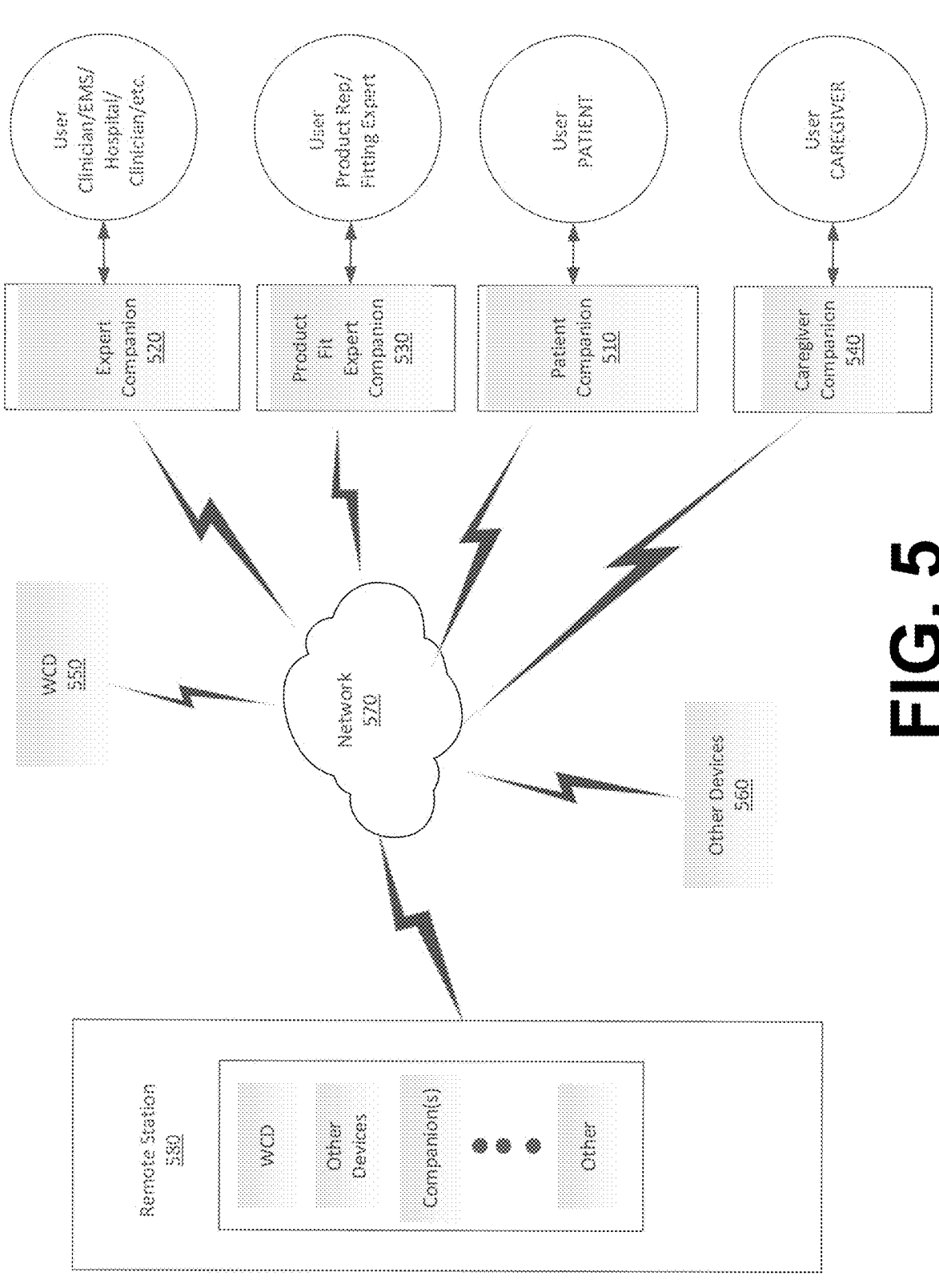
FIG. 5 is a diagram showing a companion accessory environment, including a WCD system, according to embodiments.

FIG. 5 illustrates companion embodiments 510, 520, 530, 540 and companion environment. In one embodiment, one or more companions 510, 520, 530, 540 can be integrated into a system, which can include one or more user-type-based companions 510, 520, 530, 540, sensors or other devices 560, and a medical device, such as a WCD 550. A companion is integrated when the devices within the system can recognize each other and interact either via a remote station 580, over a network 570, via a Wi-Fi, cellular, or satellite, or directly with each other, when for example within communicable proximity of one another. In embodiments, remote station 580 can include one or more of servers, cloud-based applications, and/or other computing systems. A companion can be customized to interact with devices such as medical and/or non-medical monitoring devices, for example, a non-medical tracking device, an oxygen saturation sensor, IoT device, etc.

FIG. 5, illustrates an embodiment of a companion networking system, which includes a remote station 580. The remote station 580 can provide remote monitoring access and configurations for clinicians, EMS, fitting experts, hospitals, field service representatives, nutritionists, or other consultants overseeing patients or clients, health insurance entities, and other users/stakeholders, etc. The remote station 580 is configured to interface with one or more types of companions, for example a patient companion 510, which is configured for use and needs of a patient; an expert companion 520, configured for use and needs of a clinician or EMS staff or hospital; a product or a fitting expert companion 530 configured for use by a product representative, for example a WCD product representative and/or a WCD product fitting expert; or a caregiver companion, which is configured for use by a caregiver to the patient of the WCD product system. The remote station 580 can also include other modules, such as a WCD module, configured to receive information from at least one WCD 550. The remote station 580 can also include other modules, which can be configured for insurance, billing, customer relations data and processes, user engagement database, goal options and choice menus, and so on.

Figure 6:
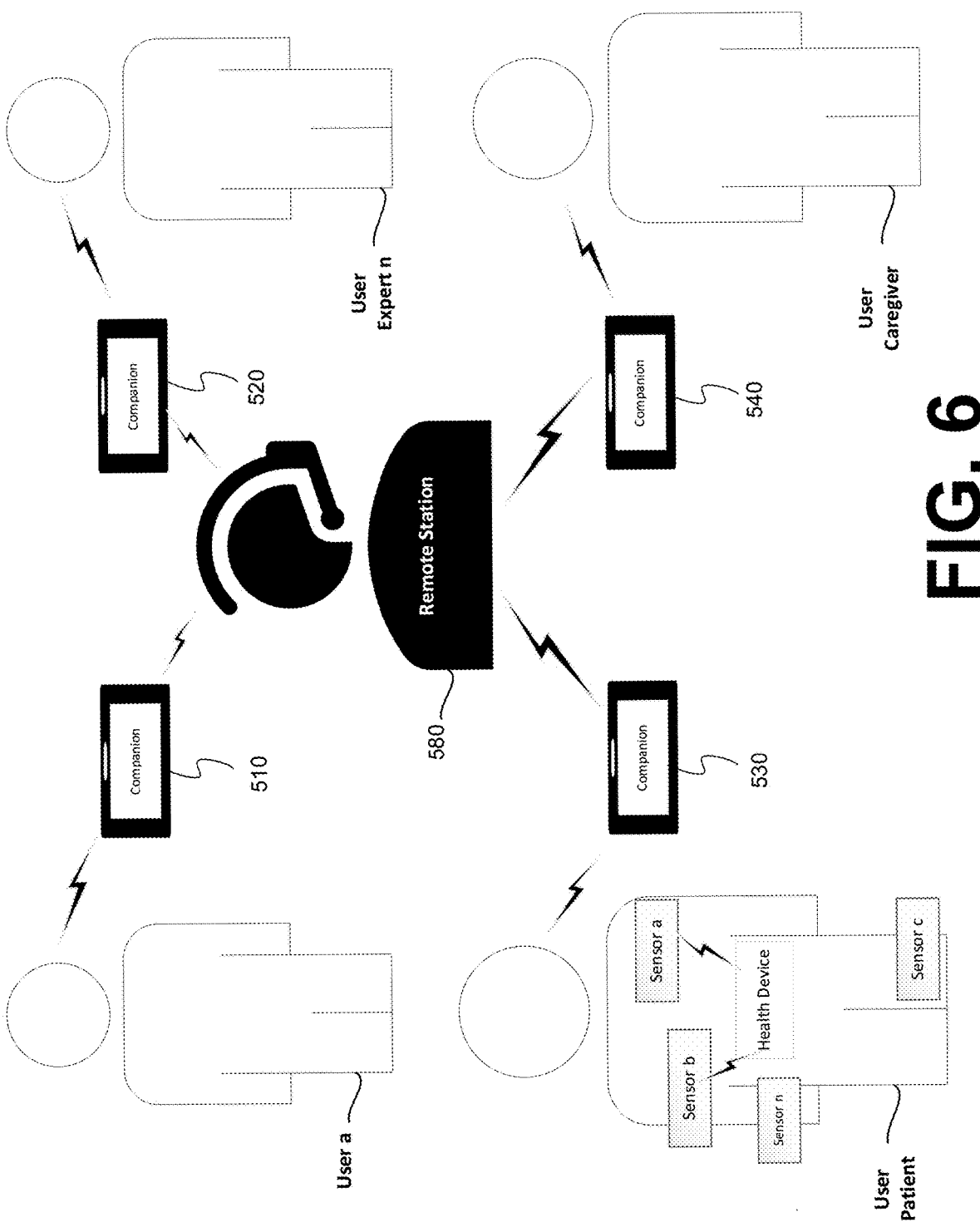
FIG. 6 is a diagram showing a companion environment, according to embodiments.

FIG. 6 is another view of the companion and companion network. As mentioned, a companion can be customized based on type of a user. For example, a companion 520 can be configured to the needs and function of an expert who can be a clinician, or a hospital, or EMS differently from that of a companion 530 which is intended for use by a patient. Similarly, a companion 540 may have different settings, for example, from those of companions 520 and 530, because companion 540 is configured for use by a caregiver. Other types of users can have companion 510 configured to their user type. In one example, an expert overseeing one or more WCD patients has a companion 520 that is configured to provide information for each of the patients, overview of ECG readouts, annotations, patient status, physiological and medical information, medical expert terminology, episode data, etc. A companion 530, on the other hand which is configured for a use by a patient, can include lay person language information, wear encouragement, reminders for prescription adherence, activity encouragement, etc. Yet for a companion 540 configured for a caregiver who may be a family member, different type of information may be appropriate, such as notifications that wear compliance is not met, alerts related to events or patient related information useful to help caregiver support the patient, etc.

The remote station can also provide central companion nexus 580 for one or more companions supporting one or more user types. As discussed further below, one user type companion 510 can have different goals from that of a companion for experts 520 such as an EMS, clinicians, hospitals or a caregiver companion 540 which may play a supportive role for one or more patients.

FIG. 7 shows sample components of a companion 700. The companion device system 701 comprises a user interface 780, a companion communication module 790, and a companion processor 730. The communication module 790 is configured to communicate with a monitoring device system 781. In one example, the communication module of the companion 790 communicates with the communication module 290 of the WCD, shown in FIG. 2. The communication module 790 of the companion can be configured to also communicate other devices or sensors 719. In one example, if the processor's machine learning (ML) module 732 determines that the input data received from at least one of the user 782 via the user interface 780, the monitoring device 781, and other device or sensor 719 is inconsistent with previously processed data according to the memory module 738 and/or the population data module 739, the companion will attempt to engage the user 782 via and the user interface 780. In a further embodiment, if the processor 730 does not receive communication input from at least one of the user 782, the monitoring device 781, and the sensor 719 for a longer than the expected cadence, which can be a preset threshold or a machine learned time period, the companion 700 is configured to initiate engagement with the user 782. The companion can be configured to communicate with a remote station, and/or other companion devices in the network using the communication module.

In embodiments, the companion 700 can be implemented into a variety of physical forms, including a mobile device such as companion 110, shown in FIG. 1, hands-free gadgets, forms capable of navigating and moving with the user, including autonomously or by being more directly controlled by the user, such as a walker, a user controlled bot or a drone, etc. The companion can be configured to assess the user from one or various vantage points and learn over time to recognize the user's face or other idiosyncrasies, preferences, habits, and also physical and/or emotional cues that could be indicative of emotional and/or physical cues/state of the user. It could also provide environmental cues as to someone's situation or whereabouts that could concern user safety, for example.

As illustrated in FIG. 8, in some embodiments, the companion can be virtual or augmented reality avatar. The avatar can be enabled via an app, which can be implemented in a variety of different physical forms, including but not limited to a mobile device, a tablet, a computer, a lens, hearing device, or AR/VR glasses, a drone, a watch, and so forth. The avatar can be further customizable and may include a photo, static or animated avatar, an avatar that can demonstrate certain exercises or activities, a cartoon-like avatar, patient's own voice or someone else's voice. In some embodiments, as illustrated in FIG. 8, a user can interact with a mobile app, which includes an animated avatar conversing with the patient.

Based on an objective/goal, the companion can offer, but is not limited to, at least one or more of the capabilities mentioned herein. The companion can be programmed to engage in human-like voice interaction and obtain answers to what could be mundane surveys or particular answers related to wellbeing of the individual patient in a fun, engaging, entertaining way, and then convey patient responses to a caregiver, a central station, or rescuers. When compliance is an objective, the companion can, for example, inquire about patient wearing the device, patient's comfort, and/or can help with suggestions or ideas for improved wearing or using of these devices, and therefore, patient compliance. The companion can suggest adjustments, or information on what to expect next, respond to issues or questions, encourage and reward for wearing the device, provide observations and suggestions based on the history of wearing the WCD, etc.

The companion can be configured for interactive engagement with a user regarding one or more, or a variety of goals or tasks, including follow-up reminders based on instructions for use of other systems/devices, Quick Start and/or Other Guides on WCD and Accessories Product(s). The companion can provide guidance and walk a user, or wearer of a health/medical system, customer, a patient through the process of setting up the product step by step, for example by use of an app, as shown in FIG. 8, including, but not limited to, unpacking a WCD from the box; charging the WCD battery; installing the cable in a garment of the WCD; laundering the garment, preparing to ship the system back in the box after use, etc.

Once the WCD is on the individual and set up, the companion can assist and engage the wearer throughout the wear period, including follow ups/reminders to the patient by sending time-appropriate messages, for example:

Your battery is at 30%, would you like to charge it now?

It appears, your garment has not been taken off for more than 24 hours, would you like to washi your garment?

Would you like me to show you how to do this?

Do you need help?

What kind of help do you need?

The Companion can ask: Do you need to contact the manufacturer?

The Companion could ask: Do you need to contact your doctor?" or

"Would you like me to get you a fitting expert?

The Companion could say: Your sensor is telling me your ECG is off, would you like help with it?

The Companion could store all pertinent contact information (doctor's numbers, hospital, insurance/Medicare info, MY Assure Number, etc.) and display it on the screen on command.

A user companion can be configured to provide a number of Wellness Prompts including, for example:

Be sure to Hydrate. Drink 8 oz of water now.

Check your pulse.

Get some fresh air.

Talk a Walk.

Meditate for 5 minutes.

Let me hear you take three deep breaths.

Can you cough and let me hear it?

Let me take a look at your eyes.

Let me take your temperature.

Etc.

The companion then can track and engage when one of the data sets has not been obtained or acted upon by a user. The companion can have a positive reinforcement messaging when milestones are achieved or wearability complied with.

In one example, based on information received from other sensors in the system, the companion can learn that a person has not changed physical position for a longer than recommended time and reminds the person or encourages the person to go to the kitchen and get some water or to do a yoga stretch or go for a walk and recommend a walking route to further encourage or entice the person, etc.

Additionally, the companion can be configured to provide a number of inspirational messages of encouragement on patient's progress including, for example:

Great job! You walked # steps today!

Fantastic! You wore your WCD 22 hours!

Smile! Your heartbeat is beautiful.

The companion can learn habits, gestures, and repeated interactions with the user over time. It can learn the user's facial and body expressions. It can be configured to recognize an expression of pain, laughter, scream, crying out for help, smile, apathy, anger, muscles spasms, facial movement or lack of movement, eye movement, whether the skin looks off, for example coloration appears ashen or lifeless indicating a warning departure from the typical skin tone, etc. It can recognize changes in patterns in a person's gait, sudden erratic movements, shaking, walking tempo, stepping patterns. It can detect and recognize if a person is wheezing, coughing, sneezing, talking, shouting, whispering.

The companion can be programmed to detect and discourage bad habits such as putting hands to face too often or not sneezing into elbow or napkin, etc. For example, when it detects a sneeze, it could say:

Gesundheit! Did you sneeze into your elbow?

And expect the response. If the response is—Yes, then say something like—Excellent and give a person some type of reward. If the response is —No, it could do something funny, for example tell the person it is taking away 10,000 points unless the person solves a puzzle or a riddle that's about sneezing into the elbow or tell a joke and order the person to go wash their hands.

Based on the information it receives, sensor and/or user input, the companion can adjust its reactions, engagement, and recommendations. For example, if it detects sadness or crying expressions, it can self-activate to ask the person:

"Oh, no! Are you crying? Can you tell me what brought that on?" or something to that extent and can base its recommendations or conversation based on what the person's response is.

The companion can ask the patient if he/she has taken medication at the same time every day and/or request that the patient tell it whether they had or not.

It could also display visuals of the medications that need to be taken.

It could warn against counterindications or side effects.

It could let the patient know when their medications are ready for pick up at a pharmacy or clinic, etc.

The companion can carry a conversation, for example ask the person how their day is going, what's new, how they are feeling, would they like to hear about the news, weather forecast, etc.

Based on such, or similar, questions, a clinician can review and further adjust monitoring and care aspects, techniques. The companion can serve as a proxy for a clinician or caregiver who may send questions or general or more specific inquiries to the patient via the companion, and/or through the care station. A clinician could send condition or patient-relevant questions to the companion and the companion can then convey them to the patient and back to the clinician or doctor when it is more convenient or appropriate, and without the need to schedule an office visit. A patient can use the companion to call doctor's office.

The companion can be configured to perform tasks a personal assistant or appointment scheduler or a reminder would traditionally perform. The companion can perform some tasks traditionally done by a caretaker, an emotional supporter, a behavior motivator. It can be configured to take on tasks a friend or family member or caregiver would traditionally perform, such as remind the user to eat, to exercise, and offer suggestions for recipes or restaurants, or types of exercise. It could analyze what the user had in the last five or so days or yesterday and offer suggestions for a more complete nutritional options for the next meal.

The companion can learn about the user's likes and dislikes, hobbies, interests, mobility level over time and can suggest topics and offer information of interest to the individual within one or more categories. Suggestions can be sensitive to, and take into account, the individual's condition, health concerns, allergies, likes and/or dislikes and other preferences.

The companion can alleviate loneliness or depression, help combat unhealthy dependencies or addictions, spot depression, suicidal risks, and promote or facilitate obtaining help. It can provide attention to the person when nobody else is around.

The companion can be configured to offer cheerful or humorous remarks, jokes, reads, games, activities, etc., which can be tailored to the individual's taste and preferences and can evolve as the companion learns about the person's preferences.

In further embodiments, the companion can serve a wide demographic. It can be assigned to a child who is developing social skills or language skills, or to a person who lives alone or a person who may suffer from loneliness or depression. The companion, by staying with a person over time, can be simply a device to talk to, or a device/gadget that can perform more other or more complex functions. The companion would be specifically tailored to the individual and his/her situation and may aid in care of the person in human-like ways.

In one example, the patient wearing the WCD may suffers from dementia or depression. In another example, a patient may have suffered a stroke and is trying to regain damaged capabilities or mobility. The companion can be configured to interact with the patient and help the patient's cognitive abilities by games and memory exercises, etc. The companion could assist with promoting, encouraging certain actions, observing the patient execute those actions, spotting trends, changes or progression and refining its suggestions based on interactions and any deviations from trends or patterns.

The companion can be configured to recognize the individual it is assigned to by, for example, using biometric indicators, including facial recognition, speech recognition, posture or gait, or other personal signatures associated with the individual. Alternatively, or in addition, the person may have a code to activate or deactivate the companion. A code could be a gesture, a tap, a password, etc. The companion can recognize and distinguish the person assigned to it over anyone else or environmental noise. The companion can call the patient by their name or nickname. The companion can be configured to communicate via verbal and/or non-verbal means. For example, non-verbal cues can include shaking of the head yes or no, pointing, tapping, waving, smiling in a certain way, or pointing, or some other personal idiosyncratic signature.

Companion can self-activate and engage its assigned individual by making a statement or asking a question or otherwise start a conversation. In one example, the companion can initiate a conversation, for example, say, sound or display something funny after a long period of time passes in which the person has not spoken, to evoke a reaction, and potentially engage the person in a conversation, or to conduct a survey in a more human-like interactive manner, or play trivia game, or offer some other fun or interesting activity, exercises, etc. In cases where non-visual or auditory communication is less preferred or where hearing or sight, or both are impaired, the companion can initiate communication by vibration, haptic, tactile means or some combination thereof.

The companion can be activated by the person's voice, and/or other features, whether a switch or a tap, or in response to environmental stimuli, such as light or noise, or room temperature, or an external call, an inquiry from a caregiver, clinician, remote station, etc.

The companion can be configured to activate based on another sensor's alert, for example a wearable sensor's, detection of a sudden deterioration in condition, and can let the patient know about the change and ask whether the patient wishes to call doctor's office or central station for help or medical advice.

The companion can also be instructed to stay quiet and not interrupt for a period of time and not interject during certain times or when other people are present, for example.

In yet another scenario, if the companion is in a form of a drone, for example, the drone can mimic human-human interactions or remind a patient that it is time to take medication. If it detects a non-emergency event when a person it is assigned to has not spoken for an extended period of time or has not substantially moved from one position for too long of a time period. The interaction can be customizable to the person's preferences and with time, the drone would "machine learn" and improve. For example, it would know not to ask—how was your day today? because this individual does not appreciate such a question. Instead, it would know to ask questions or provide trivia and/or jokes that would be of interest to the person, but requires some sort of response, whether it is a laughter, spoken answer, or a movement, that is an auditory or visual response. With time, the drone can improve using machine learning and interactions between it and the user/patient. Such drone would be able to hold conversation and redirect one's attention to a potentially more positive, happy, funny events, thoughts, actions.

In one embodiment, the companion can pick up words the patient uses frequently, or word patterns and form questions, offer statements, suggestions, games using these words. For example, when words indicate a point of interest, concern, or amusement, laughter, and in another example, it can pair the words with patient's visual expressions, such as pain, laughter, smile, sadness, etc.

The interaction can be further customizable by the person to whom companion is assigned. For example, the companion would be told to never engage in small talk, as requested by the user because this individual does not appreciate it. Instead, it would know to ask questions or provide trivia and/or jokes that would be of interest to the person, but requires some sort of response, whether it is a laughter, spoken answer, or a movement/gesture, facial expression, that is an auditory or visual response.

The companion could be further configured to execute user's requests, including physical requests, such as go check if the door is locked for the night, or bring the patient a walking support or cane, or water.

The companion can be activated based on sensed thresholds or alerts sent by other devices it can interface with. Examples of devices that can interface with the companion include external, implantable, and semi-implantable devices and system and include but are not limited to: Wearable devices such as a wearable cardioverter defibrillators (WCD), ECG monitors, heart rate monitors, heart pacing devices, blood pressure monitors, pulse oxygenation sensors, hemodynamic sensors, AF burden sensors, heart sound sensors, sleep sensors, posture or gait sensors, apnea sensors, glucose sensors, temperature sensors, transthoracic impedance sensors, moisture or perspiration sensors, proximity sensors, GPS locators, sensors configured to detect chemical or DNA components, viruses or bacteria on person's skin, hair, clothes, etc., environmental sensors configured to detect ambient temperature, humidity, air quality, pollen, radioactivity, sensors to detect presence of a harmful substance, for example harmful gases, carbon monoxide, methane, etc., sensors, devices, systems can be implemented for an average person during an activity, such as travel, exercise, large group congregations, contact tracing, etc.

In one scenario, the companion can assist with assessing and determining other device's or system's issues. For example, if another device issues an alert, or a sensor no longer adheres properly to the skin, the companion can let the patient know to and see if the patient can correct it or whether external help should be called.

Figure 9:
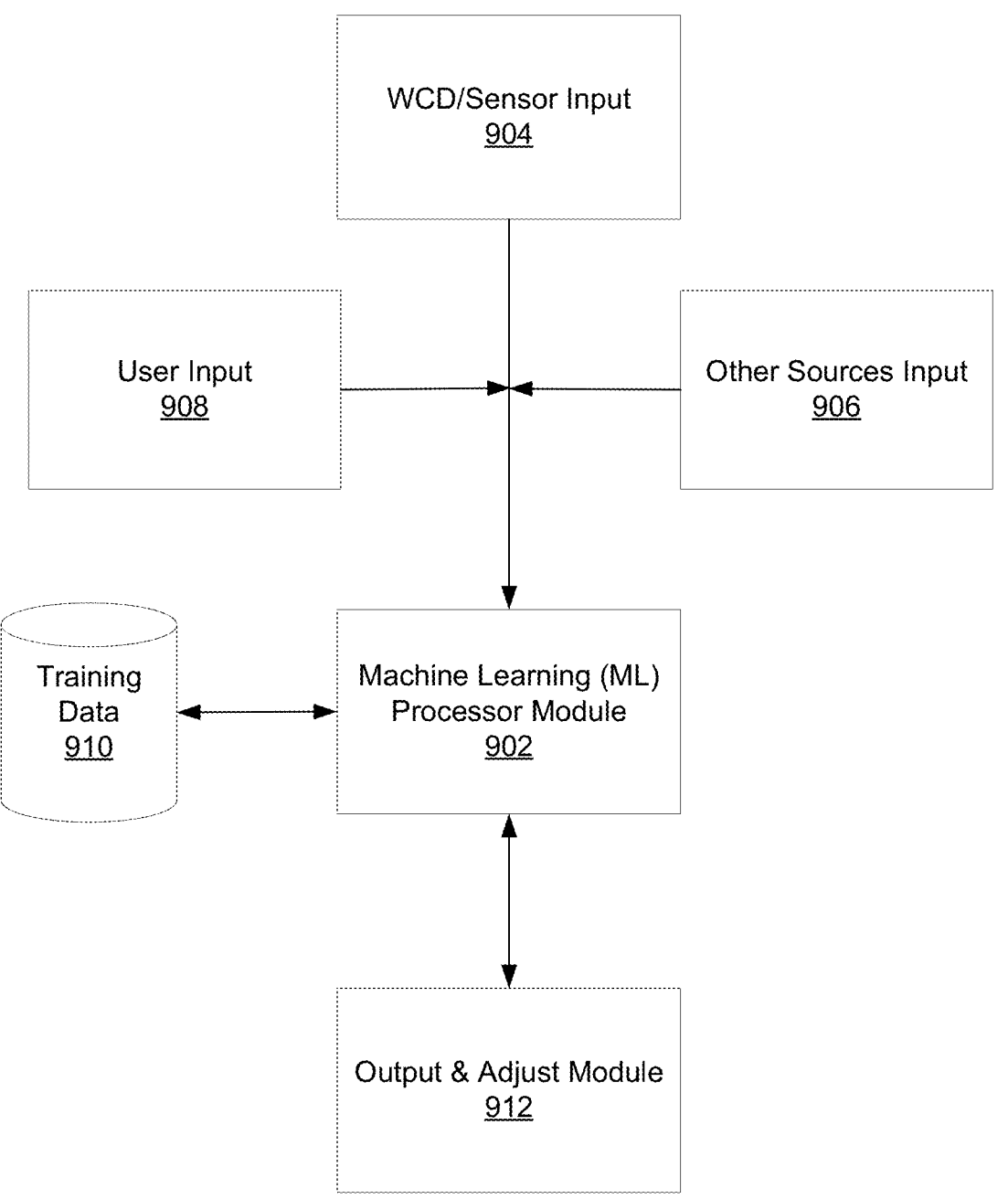
FIG. 9 is a conceptual diagram generally illustrating a machine learning that may be implemented by various embodiments of the present disclosure.

FIG. 9 is a conceptual diagram generally illustrating a machine learning system that may be implemented by various embodiments of the present disclosure. Generally stated, various embodiments may implement machine learning to automate and accomplish various goal-oriented functions. Specific illustrative, non-exhaustive examples of such embodiments are provided in this document for completeness. These and other embodiments will be apparent to those skilled in the art upon a detailed review of this discussion.

To begin, a machine learning processing module 902 receives input from various sources, such as data from various sensors 904, including WCD sensors or external sensors, described above, and/or other sources 906 such as a remote station as described with respect to FIG. 5, for example, and/or user input 908. The information received from a sensor 904 may include sensed or monitor patient parameters such as patient physiological parameters, system parameters and/or environmental parameters.

As is described with regard to a companion device, the processor module 902 can utilize input data about an individual associated with a wearable system and/or input associated with individual user feedback. Identified input data is collected and processed over a period of time. The input data can include visual and/or auditory data, which can include images, video, and/or voice recognition and speaker data. In some embodiments, the companion is used to recognize the user's voice for implementing voice recognition, activation and control. For example, the patient may use a voice command to ask for assistance because the patient is not feeling well. The processing module 902 can be utilized by the companion to target an objective or a goal, as illustrated and described but not limited to the examples provided herein, and based on the objective, the processing module can analyze patterns and trends and further utilize predictive outcomes and responses to then proactively interact with a person the wearable system and/or the companion is assigned to. The machine learning processing module 902 may receive additional information from, for example, a user interface 908 or other input mechanism (e.g., communication link to a remote data source). Examples of such additional information may take the form of instructions or data provided by a user, either a local user or a remote user, that the processing module 902 may use for machine learning.

Once input data is received, the processing module 902 performs machine learning operations to improve, predict, and/or control operations to be performed. Various specific examples of such operations will become apparent to those skilled in the art from the present disclosure. For the purpose of this general discussion, the operations performed by the processing module 902 may take any form, such as making determinations regarding whether to engage a patient or a non-patient companion user or encourage a patient or non-patient companion user to perform certain activity such as for a patient, for example, to comply with prescription, wear the WCD continuously or as continuously according to the goals.

Using machine learning methods, the processing module 902, is configured to receive at least one of input 904, 908, and/or 906 and process the input. The processed input is expected to match a projected by the ML processor output. If there is a mismatch or nonalignment, an engagement attempt with the user via a user interface, such as user interface 780, shown in FIG. 7, is made by the companion. In some embodiments, the user can override the proposed adjustment/or change. In some embodiments, a technical staff or an expert can override the proposed adjustment. In some embodiments, the adjustment can be overridden by an expert command or programmed to be overridden if such adjustment is undesirable or if certain thresholds are met. If not overridden, the output and adjust module 912 is then configured to adjust the ML processing method, and implement the adjusted method in future input processing.

Many various features and functions may benefit from the processing by the processor module 902. As adjustments are made, the process 900 may return to the data input portion of the process 900. In this manner, the processor module 902 is continually receiving input data, making adjustments to the system and/or process, engages a user and provides recommendations or advice to the user, and further refining additional adjustments. Still further, training data 910 may be used by the processor module 902 either to initially train the processor module 902 prior to use, and later, to improve the efficiency, accuracy, and operation of the processor module 902.

In another embodiment, the machine learning processor module 902, upon not receiving WCD/Sensor input, or a certain expected quality of the input, for a period of time, may cause the interface of the companion device to proactively begin to engage the user to remedy wear issues. In one example, a patient may be wearing a WCD but not realizing that a lead, as discussed in more detail above with respect to FIG. 4, is off or not functioning properly and the channel is too noisy. In another example, a patient may feel frustrated or uncomfortable and not wearing the WCD altogether. In such cases, input quality or lack of input from the WCD can be also informative input data as well. The companion can then begin to engage with the user with the goal of remedying the issue and achieving compliance and quality. Furthermore, if the user is not responsive, the companion device may initiate a type of communication indicative of prescription non-compliance with a remote caregiver, technical support, a clinician, or a remote care station location with a capability to check in on the WCD issue and the user.

The processor module 902 of the companion can look for patterns or trends and frequency of the previously received and processed data. The previously processed data can include information relating to occurrences of lack or insufficient data or quality of data transfers. In some embodiments, the companion is programmed to expect scheduled notifications of data transfer.

The machine learning module within the processor module 902 of the companion device can be configured to perform supervised and/or reinforced analysis to analyze data based on a function or an objective, and/or unsupervised learning where it can reach a conclusion based on patterns, track record, trial and error.

Machine learning may include, but is not limited to, supervised learning, unsupervised learning, nature inspired learning, statistical learning, product use learning, reinforcement learning, etc. and further include methods such as linear regression, logistic regression, decision trees, SVM, Naïve Bayes, kNN, K-Means, Random Forest, Dimensionality Reduction Algorithms, Gradient Boosting methods. In a further example, machine learning can include deep neural learning methods.

Specific implementations of various embodiments employing processor module 902 of the companion are described in greater detail. Each of the illustrative embodiments may be implemented individually or in various combinations. Still further, other embodiments will become apparent to those skilled in the art from the following illustrative embodiments.

Figure 10:
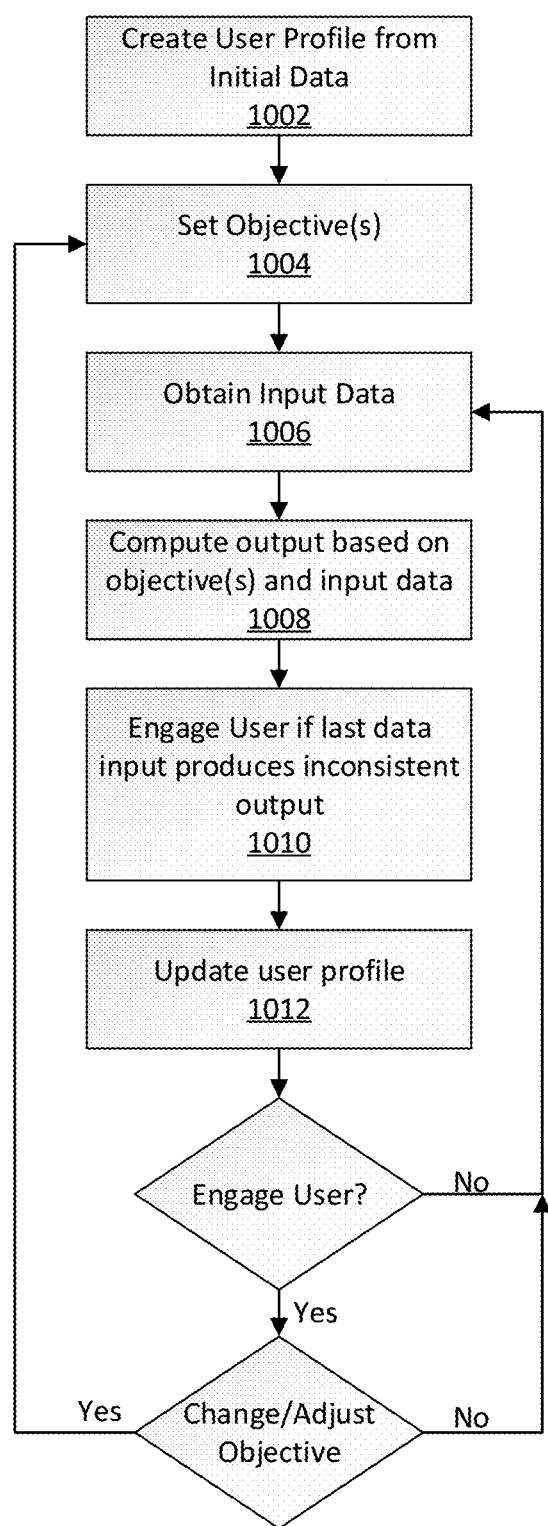
FIG. 10 is an example process diagram in accordance with embodiments.

FIG. 10 is a conceptual flow diagram generally illustrating a machine learning process that may be implemented by various embodiments of the present disclosure. Generally stated, various embodiments may implement machine learning to automate and accomplish various user goal-oriented functions. Specific illustrative, non-exhaustive examples of such embodiments are provided in this document for completeness. These and other embodiments will be apparent to those skilled in the art upon a detailed review of this discussion.

The machine learning processor module 902 of FIG. 9, can receive input data from one or more sources and make adjustments over WCD or monitoring device wear time. To initiate the process for a user, in FIG. 10, at step 1002, a user profile is created from an initial input data, which can include a patient condition or clinical input data, sensor data, family data, historical data, subjective and objective survey input data, etc. A goal or an objective is then defined for the user and set at step 1004. An example of an objective is wear compliance over the wear prescription time. At step 1006 input data is obtained for processing by the processor module, like the processor module 730 of FIG. 7 or 902 of FIG. 9, each time a WCD transfers data, or input is received via a user interface 780 or via the communication module 790. In addition, when a scheduled or projected frequency of data transfer does not occur for more than predetermined number of times, for example more than two subsequent non-occurrences of data transfer, lack of data transfer or interruptions of transfers are also input data indicative of wear and compliance and are processed by the processor. At step 1008, machine learning methods are applied to compute whether the output data is consistent with estimated or projected output, whether most recent data fits the trend, pattern. If an incongruency is detected and the input results in an output not congruous with expected output, at step 1010 engagement with a user is triggered by the processor. Matched outputs and inconsistent outputs are used at step 1012 to update user's profile and make determinations whether to engage the user, and further whether to adjust objectives for the user.

In one example, the companion's processor determines there was no data transfer out of the WCD at a scheduled time. The expected output was confirmation of data transfer and the received information indicates otherwise. When interruption in data transfer occurs on the second time in a row, the companion is configured to attempt to engage a user. The processor is configured to attempt to help the user resolve the issue by using the user's wear history and, if needed additional techniques, such as decision trees for a WCD-related wear, lead off, garment adjustment, noise issue. If the user engages in an interaction with the companion, the processor is configured to process user inputs against projected machine learning outputs. When the projected and real outputs, it manifests in next data transfer, and means that the output generated by the processor, and used as instruction for resolving the problem, resulted in the next user input that was consistent with the expected output of data transfer. User history and profile can be updated to reflect updates in the methods and whether any adjustments to any of the objectives were made.

In a further embodiment, if a third data transfer in a row does not occur, the processor is configured to trigger the communications module and engage a caregiver and/or remote station.

As described previously with respect to FIG. 9, machine learning methods include self-adjustment data input is obtained and computed at a particular frequency to produce updates in a step 1012 to set a user up with achievable and measurable goal and a plan to advance towards it.

User engagement can be determined based on some data and/or pattern/trend deviations and not on other data and/or pattern/trend deviations, and what can be ignored and what cannot be ignored by a user attention can also be adjusted with time. Using again the example above, if the companion's processor determines there was, for example, no data transfer out of the WCD at a scheduled time. For the first time, the processor of the companion will process this information as inconsistent with an expected output. When interruption in data transfer occurs on the second time in a row, however, the companion is configured to now attempt to engage a user. The processor is further configured to attempt to help the user resolve the issue by using the user's wear history and, if needed additional techniques, such as decision trees for a WCD-related wear, lead off, garment adjustment, noise issue. If the user engages in an interaction with the companion, the processor is configured to process user inputs against projected machine learning outputs. When the projected and real outputs, it manifests in next data transfer, and means that the output generated by the processor, and used as instruction for resolving the problem, resulted in the next user input that was consistent with the expected output of data transfer. User history and profile can be updated to reflect updates in the methods and whether any adjustments to any of the objectives were made.

In a further embodiment, if a third data transfer in a row does not occur, the processor is configured to trigger the communications module and engage a caregiver and/or remote station. The remote station can then have an expert, for example a technician, or a fitting expert, or a caregiver check up on the patient to determine whether a noncompliance issue can be resolved.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

What is claimed is:

1. A method of using a user support companion device with a Wearable Cardioverter Defibrillator (WCD) system, the method comprising:

generating a profile of a user of the user support companion device from initial input data, wherein the initial input data includes at least a patient condition or clinical input data of the user using the WCD system, the user support companion device including a virtual companion implemented using one or more machine learning methods, wherein the virtual companion is a customizable avatar;

receiving a goal for the user of the user support companion device, wherein the goal comprises a WCD wear time corresponding to a minimum daily amount of time the user has worn the WCD system;

receiving, from the WCD system, data indicative of the WCD wear time, the data comprising user input data and/or data generated by the WCD system;

determining, from the received data, a metric of a progress of the user toward the goal;

determining whether the metric is indicative of the user not meeting the goal; and responsive to a determination that the metric is indicative of the user not meeting the goal, communicating with the user using the virtual companion to motivate the user to take an action for achieving the goal, wherein the communication is based, at least in part, on the generated profile.

2. The method of claim 1, wherein determining whether the metric is indicative of the user not meeting the goal further includes:

using, by the one or more machine learning methods, information in the received data that is indicative of whether the user took the action communicated to the user in a previous communication by the virtual companion that is based on artificial intelligence to motivate the user to take the action.

3. The method of claim 1, wherein determining whether the metric is indicative of the user not meeting the goal comprises computing, by applying the one or more machine learning methods, that output data associated with the WCD wear time in the received data is inconsistent with projected output data.

4. The method of claim 1, wherein determining whether the metric is indicative of the user not meeting the goal comprises determining whether the received data indicates the user has not worn the WCD system for a predetermined duration.

5. The method of claim 1, wherein determining whether the metric is indicative of the user not meeting the goal comprises determining one or more of: no data is received by the user support companion device from the WCD, data transfer between the user support companion device and the WCD system is interrupted, data is not received by a remote station from the user support companion device, and the received data is determined to be noisy by one or more of the WCD system, the user support companion device, and/or the remote station.

6. The method of claim 1, wherein the received data includes data indicative of one or more activities performed by the user.

7. The method of claim 1, wherein the virtual companion is configured, based on the generated profile, to interact with the user using a cheerful remark.

8. A wearable system, comprising:

a wearable cardioverter defibrillator (WCD); and a user support companion device comprising:

means for implementing a virtual companion using one or more machine language methods, wherein the virtual companion is a customizable avatar;

means for generating a profile of a user of the user support companion device from initial input data, wherein the initial input data includes at least a patient condition or clinical input data of the user;

means for receiving a goal for the user of the wearable system, wherein the goal comprises a WCD wear time corresponding to a minimum daily amount of time the user has worn the WCD;

means for receiving, from the WCD, data indicative of the WCD wear time, the data comprising user input data and/or data generated by the WCD;

means for determining, from the received data, a metric of a progress of the user toward the goal;

means for determining when the metric is indicative of the user not meeting the goal; and means for, responsive to a determination that the metric is indicative of the user not meeting the goal, communicating with the user using the virtual companion to take an action for achieving the goal, wherein the communication is based, at least in part, on the generated profile.

9. The wearable system of claim 8, wherein the means for determining when the metric is indicative of the user not meeting the goal further includes:

applying the one or more machine language methods to information in the received data that is indicative of whether the user took the action communicated to the user in a previous communication by the virtual companion to motivate the user to take the action.

10. The wearable system of claim 8, wherein the means for determining when the metric is indicative of the user not meeting the goal comprises computing, by applying the one or more machine language methods, that output data associated with the WCD wear time in the received data is inconsistent with projected output data.

11. The wearable system of claim 8, wherein the means for determining when the metric is indicative of the user not meeting the goal comprises determining one or more of: no data is received by the user support companion device from the WCD, data transfer between the user support companion device and the WCD is interrupted, data is not received by a remote station from the user support companion device, and the received data is determined to be noisy by one or more of the WCD, the user support companion device, and/or the remote station.

12. The wearable system of claim 8, wherein the data generated by the WCD includes data indicative of one or more activities performed by the user.

13. The wearable system of claim 8, wherein the virtual companion is configured, based on the generated profile, to interact with the user using a cheerful remark.

14. The wearable system of claim 8, wherein the avatar is customized, using the one or more machine language methods, based on previous responses of the user to interactions with the avatar.

15. The method of claim 1, wherein the virtual companion is configured, based on the generated profile, to interact with the user using a remark that is tailored based on preferences of the user.

16. The method of claim 1, wherein the virtual companion is configured, based on the generated profile, to interact with the user using a joke.

17. The method of claim 1, wherein the virtual companion is configured, based on the generated profile, to interact with the user using a game.

18. The wearable system of claim 8, wherein the virtual companion is configured, based on the generated profile, to interact with the user using a remark that is tailored based on preferences of the user.

19. The wearable system of claim 8, wherein the virtual companion is configured, based on the generated profile, to interact with the user using a joke.

20. The wearable system of claim 8, wherein the virtual companion is configured, based on the generated profile, to interact with the user using a game.

* * * * *